(12) United States Patent
Lafyatis et al.

(10) Patent No.: US 7,605,295 B1
(45) Date of Patent: Oct. 20, 2009

(54) INTEGRATED PROCESS YIELDING XYLENES FROM MIXED AROMATICS

(75) Inventors: David S. Lafyatis, Schaumburg, IL (US); Edwin P. Boldingh, Arlington Heights, IL (US); Antoine Negiz, Wilmette, IL (US); Edward M. Casey, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/146,865

(22) Filed: Jun. 26, 2008

(51) Int. Cl.
  *C07C 6/12* (2006.01)
(52) U.S. Cl. ..................................... 585/475
(58) Field of Classification Search .................. 585/475
  See application file for complete search history.

(56) References Cited

U.S. PATENT DOCUMENTS

| 6,040,490 A | 3/2000 | Ichioka et al. ............... 585/475 |
| 6,060,417 A | 5/2000 | Kato et al. ..................... 502/66 |
| 6,486,372 B1 | 11/2002 | Merlen et al. ................ 585/467 |
| 6,740,788 B1 | 5/2004 | Maher et al. ................. 585/319 |
| 7,109,389 B2 | 9/2006 | Kong et al. .................. 585/302 |
| 7,202,189 B2 | 4/2007 | Negiz et al. .................... 502/74 |
| 7,220,885 B2 | 5/2007 | Boldingh et al. ............ 585/475 |
| 7,265,252 B1 | 9/2007 | Frey et al. .................... 585/319 |

OTHER PUBLICATIONS

U.S. Appl. No. 12/146,847, filed Dec. 31, 2009, Moscoso et al.
U.S. Appl. No. 12/146,831, filed Dec. 31, 2009, Boldingh et al.

*Primary Examiner*—Thuan Dinh Dang
(74) *Attorney, Agent, or Firm*—David J Piasecki

(57) ABSTRACT

The subject invention comprises an aromatics complex to improve yields from a mixed aromatics feed. Through the use of a novel catalyst having higher activity and stability in a transalkylation unit in the complex, a higher xylene yield is obtained.

16 Claims, 4 Drawing Sheets

INTEGRATED PROCESS YIELDING XYLENES FROM MIXED AROMATICS

FIELD OF THE INVENTION

This invention relates to a process for increasing the production of xylenes from a mixed aromatics feed stream. More specifically, the invention comprises a complex of units including a novel transalkylation process and catalyst to convert lighter and heavier aromatics to yield and recover $C_8$ aromatics.

BACKGROUND OF THE INVENTION

Most new aromatics complexes are designed to yield benzene and para-xylene. Benzene is a versatile petrochemical building block used in many different products including ethylbenzene, cumene, and cyclohexane. Para-xylene is also an important building block primarily for the production of polyester fibers, resins, and films formed via terephthalic acid or dimethyl terephthalate intermediates. Since the relative yields of benzene and para-xylene generally do not match the proportions obtained from aromatics-generating processes such as catalytic reforming and cracking, an aromatics complex to obtain these preferred products usually comprises a variety of processes such as one or more of transalkylation, disproportionation, isomerization and dealkylation.

An aromatics complex flow scheme of the known art is represented by that of Meyers in the Handbook of Petroleum Refining Processes, 3rd. Edition in 2003 by McGraw-Hill.

The known art includes a number of processing schemes including transalkylation for converting lighter aromatics, particularly toluene, and heavier aromatics, especially $C_9$ aromatics, to yield $C_8$ aromatics in order to increase the yield of xylenes which can be processed to obtain para-xylene from an aromatics complex. Such transalkylation processes generally are limited in the extent to which they can convert aromatics heavier than $C_9$ to lighter products, and there is a need in the industry for more effective processes in order to improve catalyst stability with higher concomitant xylene yield.

SUMMARY OF THE INVENTION

Broadly, the invention comprises a process for producing xylenes from an aromatics-rich feed stream comprising the steps of: (a) separating the aromatics-rich feed stream and a transalkylation product stream in a fractionation zone to produce a benzene-rich stream, a toluene-rich stream, a $C_8$-aromatics product and $C_9$-and-heavier stream; (b) fractionating the $C_9$-and-heavier stream in a heavy-aromatics fractionator to obtain a $C_9$-$C_{11}$+ heavy transalkylation feed and a $C_{12}$+ residual stream; and (c) combining the toluene-rich stream and $C_9$-$C_{11}$+ heavy transalkylation feed to obtain a combined transalkylation feed and contacting the combined feed in a transalkylation zone under transalkylation conditions with a transalkylation catalyst which comprises a UZM-14 aggregate material comprising globular aggregates of crystallites having a MOR framework type comprising 12-ring channels, a mesopore volume of at least about 0.10 cc/gram, and a mean crystallite length parallel to the direction of the 12-ring channels of about 60 nm or less, to produce the transalkylation product stream of step (a) having an increased concentration of xylenes relative to the combined transalkylation feed.

In a specific embodiment, the invention comprises a process for producing xylenes from an aromatics-rich feed stream comprising the steps of: (a) separating the aromatics-rich feed stream and a transalkylation product stream in a fractionation zone to produce a benzene-rich stream, a toluene-rich stream, a $C_8$-aromatics product and $C_9$-and-heavier stream; and, (b) combining the toluene-rich stream and $C_9$-and-heavier stream to obtain a combined transalkylation feed and contacting the combined feed in a transalkylation zone under transalkylation conditions with a transalkylation catalyst which comprises a UZM-14 aggregate material comprising globular aggregates of crystallites having a MOR framework type comprising 12-ring channels, a mesopore volume of at least about 0.10 cc/gram, and a mean crystallite length parallel to the direction of the 12-ring channels of about 60 nm or less, to produce the transalkylation product stream of step (a) having an increased concentration of xylenes relative to the combined transalkylation feed.

A variant of the above embodiments comprises dividing the $C_9$-and-heavier stream into a heavy recycle stream and a heavy-aromatics-fractionator feed stream and bypassing the heavy recycle stream directly to the transalkylation unit.

Another specific embodiment comprises the steps of: (a) combining the aromatics-rich feed stream with recycled heavy aromatics and a recycled toluene-rich stream to obtain a combined transalkylation feed and contacting the combined feed in a transalkylation zone under transalkylation conditions with a transalkylation catalyst which comprises a UZM-14 aggregate material comprising globular aggregates of crystallites having a MOR framework type comprising 12-ring channels, a mesopore volume of at least about 0.10 cc/gram, and a mean crystallite length parallel to the direction of the 12-ring channels of about 60 nm or less, to produce a transalkylation product stream having an increased concentration of xylenes relative to the combined transalkylation feed; (b) separating the transalkylation product stream in a fractionation zone to produce a benzene-rich stream, a toluene-rich recycle stream, a $C_8$-aromatics product and $C_9$-and-heavier stream; and, (c) fractionating the $C_9$-and-heavier stream in a heavy-aromatics fractionator to obtain recycled heavy aromatics and a $C_{12}$+ residual product stream.

Preferably the transalkylation catalyst in each of the above embodiments comprises one or more of the following characteristics: (1) globular aggregates have a mesopore volume of at least about 0.10 cc/gram, preferably at least about 0.13 cc/gram, and especially at least about 0.2 cc/gram; (2) the UZM-14 crystallites have at least about $1 \times 10^{19}$ 12-ring-channel openings/gram of UZM-14 material; (3) the mean crystallite length parallel to the direction of the 12-ring channels is about 60 nm or less and preferably about 50 nm or less; (4) The $Si/Al_2$ ratio of the UZM-14 aggregate material generally is between about 8 and about 50, and preferably is no more than about 30.

Optionally, the $C_8$-aromatics product is sent to a combination of a para-xylene-recovery process and a $C_8$-aromatics-isomerization process to obtain a para-xylene product and a $C_7$-and-lighter stream sent to step (a) for separation of a benzene-rich stream, a toluene-rich stream, and a non-aromatic product.

DETAILED DESCRIPTION OF THE INVENTION

The aromatics-rich feed stream to the process of the invention may be derived from a variety of sources, including without limitation catalytic reforming, steam pyrolysis of naphtha, distillates or other hydrocarbons to yield light olefins and heavier aromatics-rich byproducts (including gasoline-range material often referred to as "pygas"), and catalytic or thermal cracking of distillates and heavy oils to yield products in the gasoline range. Products from pyrolysis or other cracking operations generally will be hydrotreated according to processes well known in the industry before being charged to the complex in order to remove sulfur, olefins and other compounds which would affect product quality. Light cycle oil from catalytic cracking also may be beneficially hydrotreated and/or hydrocracked according to known technology to yield products in the gasoline range; the hydrotreating preferably also includes catalytic reforming to yield the aromatics-rich feed stream. If the feed stream is catalytic reformate, the reformer preferably is operated at high severity to achieve high aromatics yield with a low concentration of nonaromatics in the product. The reformate also advantageously is subjected to olefin saturation to remove potential product contaminants and materials that could polymerize to heavy nonconvertibles in a transalkylation process. Such processing steps are described in U.S. Pat. No. 6,740,788 B1, incorporated herein by reference thereto.

The feed stream to the process of the invention comprises alkylaromatic hydrocarbons of the general formula $C_6H_{(6-n)}R_n$, where n is an integer from 1 to 5 and R is one or more of $CH_3$, $C_2H_5$, $C_3H_7$, $C_4H_9$, or $C_5H_{11}$ in any combination. The feed stream also may comprise benzene and/or aromatics having from 2 to 4 rings. Suitable components of the feed stream thus generally include, for example but without so limiting the invention, benzene, toluene, ethylbenzene, meta-xylene, ortho-xylene, para-xylene, ethyl-toluenes, trimethyl-benzenes, diethyl-benzenes, triethylbenzenes, propylbenzenes, methylpropylbenzenes, ethylpropylbenzenes, diisopropylbenzenes, butylbenzenes, indanes, naphthalenes, tetralins, decalins, biphenyls, diphenyls and fluorenes. The feed stream also may contain lesser concentrations of nonaromatics such as pentanes, hexanes, heptanes and heavier paraffins along with methylcyclopentane, cyclohexane and heavier naphthenes; pentanes and lighter paraffins generally will have been removed before processing in the aromatics complex. The combined transalkylation feed preferably contains no more than about 10 wt-% nonaromatics; olefins preferably are restricted to a Bromine Index of no more than about 1000, and preferably no more than about 500.

Figure 1:
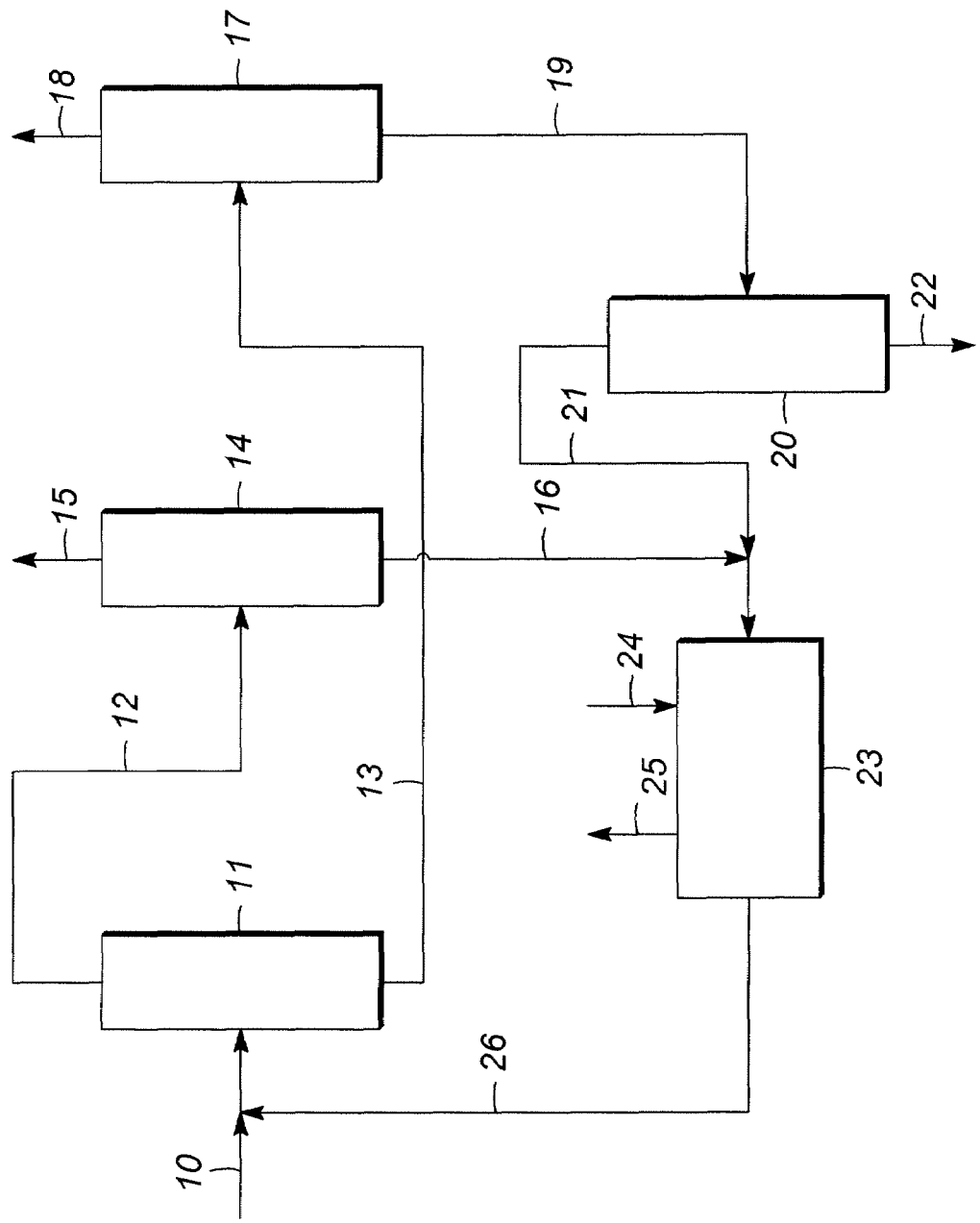
FIG. 1 is an process flow diagram illustrating the invention.

FIG. 1 is a simplified flow diagram of a broad embodiment of the present invention. The aromatics-rich feed stream 10 and a transalkylation product stream 26 are fractionated in a fractionation zone, comprising fractionators 11, 14 and 17 as illustrated in FIG. 1. Fractionator 11 separates a toluene-and-lighter stream overhead in line 12, which passes to fractionator 14 which separates a benzene-rich stream overhead in line 15 from a toluene-rich stream in line 16. A heavier-than-toluene stream in line 13 passes to fractionator 17 which recovers a $C_8$-aromatics product overhead in line 18.

There are a number of options in the fractionation zone, depending primarily on the nonaromatics content of the aromatics-rich feed stream and on product objectives. Benzene may be sent to the transalkylation zone, and a separation of benzene and toluene may not be necessary in this case. If a net benzene product is desired, then a high quality product may be obtained directly from the fractionator 14 as shown. However, if a net benzene product needs to be of very high purity; this can be effected by extractive distillation of the benzene-rich stream from fractionator 14. If the toluene-rich stream contains excessive nonaromatics, the toluene-and-lighter stream in line 12 may be processed by extraction to remove the nonaromatics. A stabilizer in the transalkylation zone can provide a benzene-rich stream suitable for charging to extractive distillation. In this event, the feed stream and transalkylation product may be fractionated separately to obtain feed to fractionator 14.

A $C_9$-and heavier stream from fractionator 17 passes to heavy-aromatics fractionator 20, which separates a $C_9$-$C_{11}$+ heavy transalkylation feed 21 (comprising 11-carbon aromatics plus optionally a portion of 12-and-higher-carbon aromatics with atmospheric boiling points of up to about 250° to 260° C.) from a $C_{12}$+ residual stream 22 (comprising biphenyls, diphenyls, fluorenes and associated components). The $C_9$-$C_{11}$+ heavy transalkylation feed favorably comprises a substantial amount of 12-and-higher-carbon aromatics; the transalkylation catalyst of the invention tolerates accompanying polycyclics which would adversely affect known catalysts. In lieu of fractionator 20, stream 21 may be obtained as a sidecut stream from fractionator 17. Streams 16 and 21 provide the combined transalkylation feed. The reaction in transalkylation zone 23 generally is effected in the presence of hydrogen, supplied in line 24, and light ends are stripped from the product and removed in stream 25. The transalkylation zone yields a product with an increased content of xylenes in stream 26 which is sent to the fractionation zone.

Figure 2:
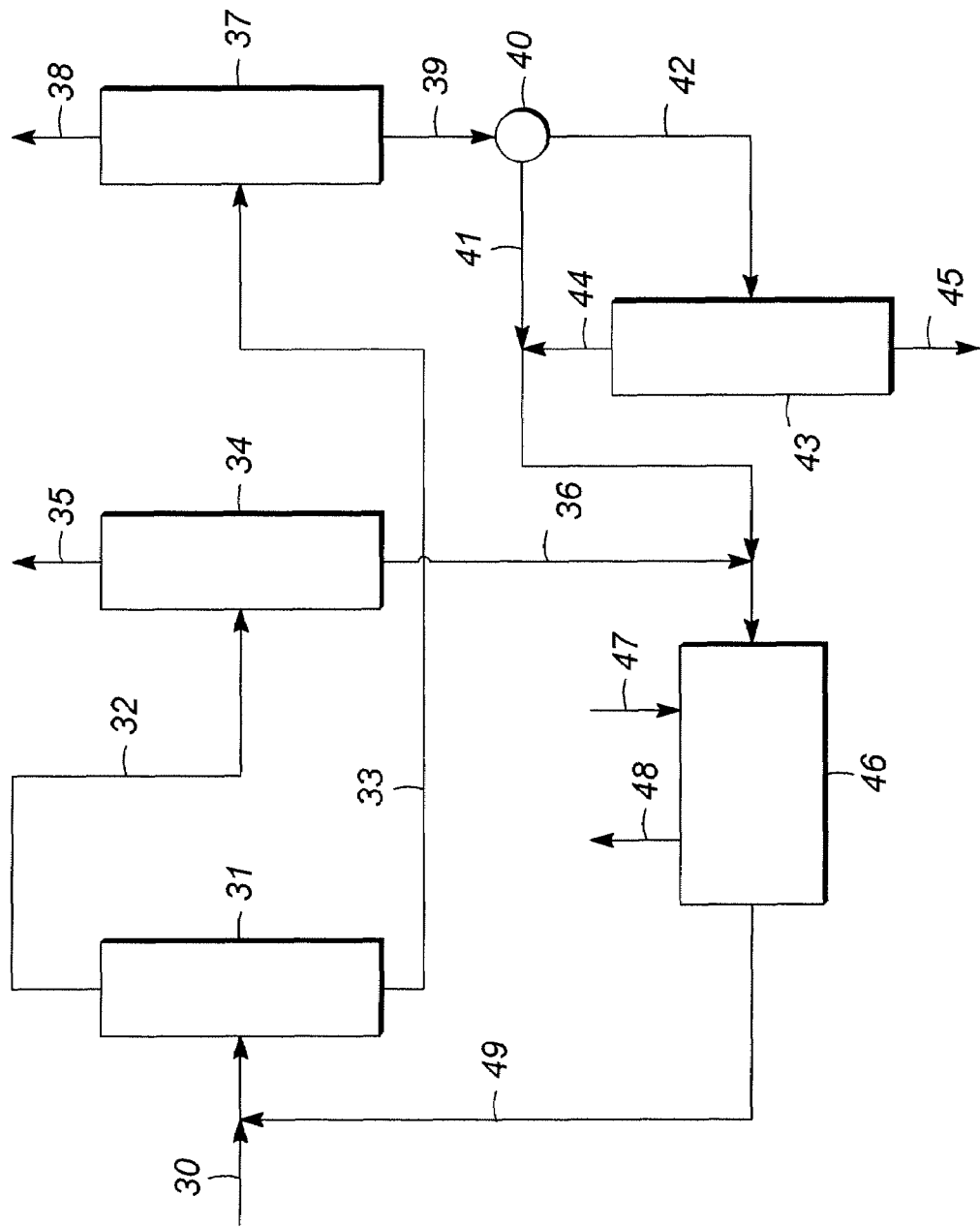
FIG. 2 is an process flow diagram of a particular embodiment of the invention.

FIG. 2 is a simplified flow diagram of a particular embodiment of the present invention. The aromatics-rich feed stream 30 and a transalkylation product stream 47 are fractionated in a fractionation zone, comprising fractionators 31, 34 and 37 as illustrated in FIG. 2. Fractionator 31 separates a toluene-and-lighter stream overhead in line 32, which passes to fractionator 34 which separates a benzene-rich stream overhead in line 35 from a toluene-rich stream in line 36. A heavier-than-toluene stream in line 33 passes to fractionator 37 which recovers a $C_8$-aromatics product overhead in line 38. The same options for nonaromatics removal apply as for FIG. 1.

A $C_9$-and heavier stream 39 from fractionator 37 passes to splitter 40, which divides the stream into line 41 as a heavy recycle stream and line 42 to heavy-aromatics fractionator 43 which separates a $C_9$-$C_{11}$+ heavy transalkylation feed 44 (comprising 11-carbon aromatics plus optionally a portion of 12-or-higher-carbon aromatics with atmospheric boiling points of up to about 250° to 260° C.) from a $C_{12}$+ residual stream 45 (comprising biphenyls, diphenyls, fluorenes and associated components). It may also be advantageous in this embodiment to take a sidecut stream from fractionator 37 which substantially contains $C_9$ and $C_{10}$ aromatics and send this stream directly to the transalkylation reactor, thereby reducing the size of stream 39 and therefore the size of the downstream heavy-aromatics fractionator 43. The proportion of stream 39 which is sent directly to transalkylation as heavy recycle via stream 41 may vary generally from about 1 to about 99 mass-%, and more usually in the range of from about 10 to about 90 mass-% depending on the nature of the heaviest portion, particularly polycyclics, of stream 39. Streams 36, 41 and 44 provide the combined transalkylation feed which thus includes a portion of the $C_{12}$+ since the transalkylation catalyst of the invention tolerates accompanying polycyclics which would adversely affect known catalysts. The reaction in transalkylation zone 46 generally is effected in the presence of hydrogen, supplied in line 47, and light ends are stripped from the product and removed in stream 48. The transalkylation zone yields a product with an increased content of xylenes in stream 49 which is sent to the fractionation zone.

Figure 3:
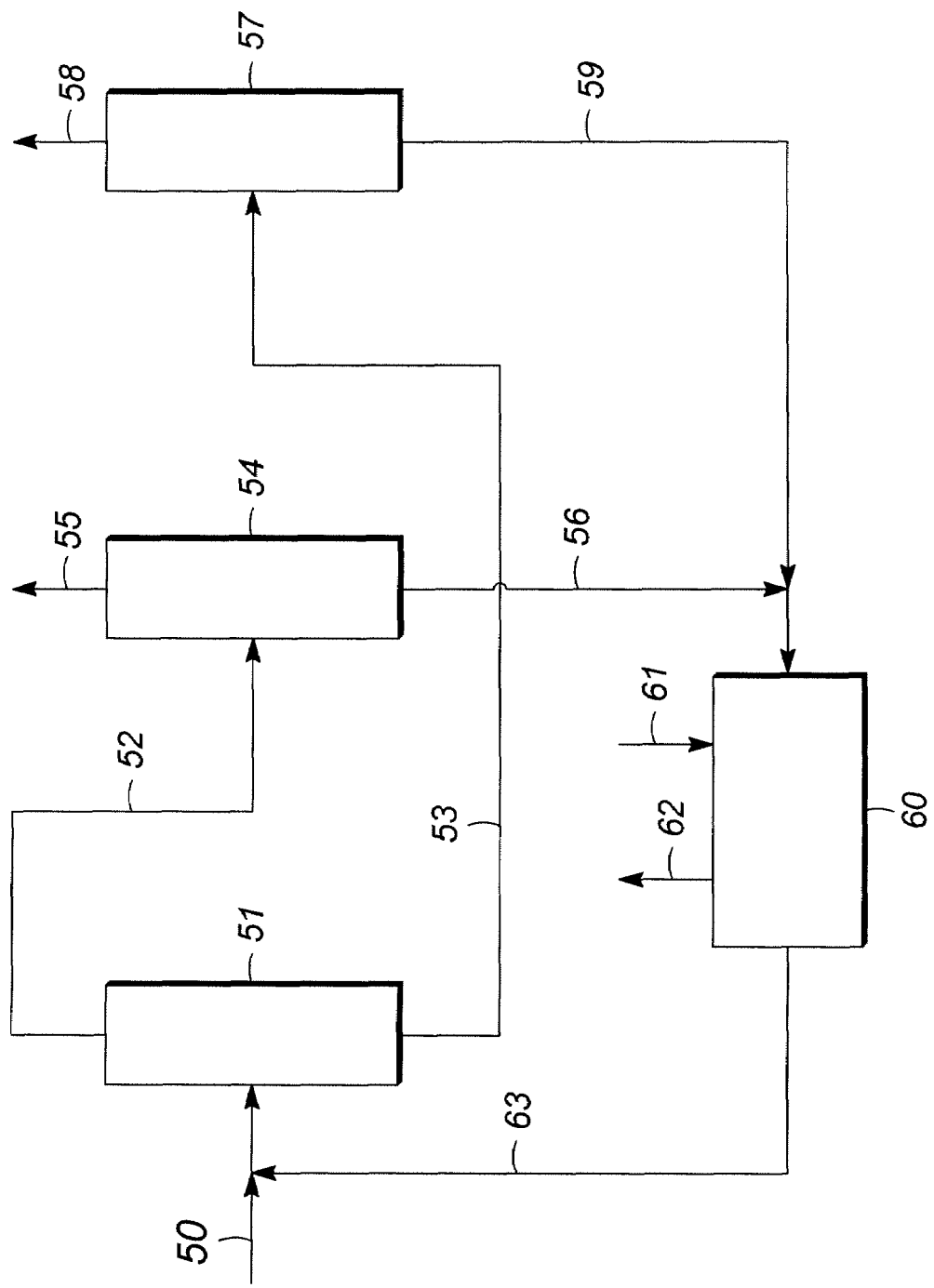
FIG. 3 is an alternative process flow diagram of a unique embodiment of the invention.

FIG. 3 is a simplified flow diagram of a unique embodiment of the present invention. The aromatics-rich feed stream 50 and a transalkylation product stream 63 are fractionated in a fractionation zone, comprising fractionators 51, 54 and 57 as illustrated in FIG. 3. Fractionator 51 separates a toluene-and-lighter stream overhead in line 52, which passes to fractionator 54 which separates a benzene-rich stream overhead in line 55 from a toluene-rich stream in line 56. A heavier-than-toluene stream in line 53 passes to fractionator 57 which recovers a $C_8$-aromatics product overhead in line 58. The same options for nonaromatics removal apply as for FIG. 1.

A $C_9$-and heavier stream 59 from fractionator 57 joins streams 56 to form the combined transalkylation feed which includes all of the $C_{12}$+ on the basis that the transalkylation catalyst of the invention tolerates accompanying polycyclics which would adversely affect known catalysts. The reaction in transalkylation zone 60 generally is effected in the presence of hydrogen, supplied in line 61, and light ends are stripped from the product and removed in stream 62. The transalkylation zone yields a product with an increased content of $C_8$ aromatics in stream 63 which is sent to the fractionation zone.

Figure 4:
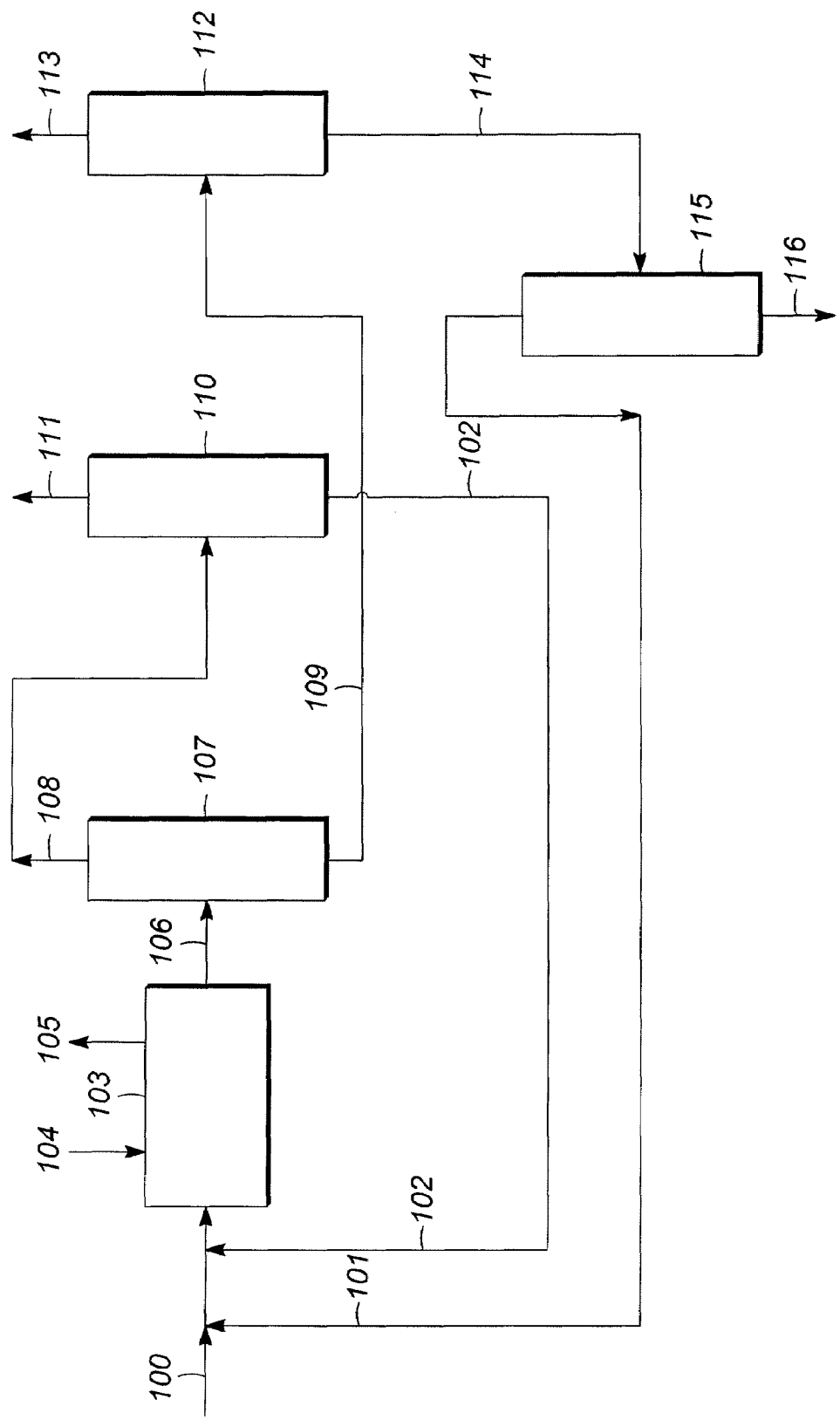
FIG. 4 is a process flow diagram of a variant of the invention.

It is within the scope of the invention that the aromatics-rich feed stream, in particular the $C_9$+ portion, is processed directly in the transalkylation unit without fractionation to remove a residual stream; this option is illustrated in FIG. 4. The aromatics-rich feed stream 100, represented here as a $C_9$+ stream optionally including toluene which has been separated by fractionation from a wider-range feed stream, joins recycled heavy aromatics in stream 101 and a recycled toluene-rich stream 102 as feed to transalkylation zone 103. The reaction in transalkylation zone 103 generally is effected in the presence of hydrogen, supplied as stream 104, and light ends are stripped from the product and removed in stream 105. The transalkylation zone yields a product with an increased content of xylenes in stream 106 which is sent to the fractionation zone.

The fractionation zone comprises fractionators 107, 110, 112 and 115 as illustrated in FIG. 4. Fractionator 107 separates a toluene-and-lighter stream overhead in line 108, which passes to fractionator 110 which separates a benzene-rich stream overhead in line 111 from toluene-rich recycle in line 102. A heavier-than-toluene stream in line 109 passes to fractionator 112 which recovers a $C_8$-aromatics product overhead in line 113. The same options for nonaromatics removal apply as for FIG. 1.

A $C_9$-and heavier stream 114 from fractionator 112 passes to fractionator 115, which separates recycled heavy aromatics stream 101 (comprising 11-carbon aromatics plus optionally a portion of 12-or-higher-carbon aromatics with atmospheric boiling points of up to about 250° to 260° C.) from a $C_{12}$+ residual stream 116 (comprising biphenyls, diphenyls, fluorenes and associated components). Options for bypassing part or all of $C_9$-and-heavier stream 114 directly to transalkylation as in FIGS. 2 and 3 also are applicable in this case.

It also is within the scope of the invention as presented in any of the schemes represented in FIG. 1, 2 or 4 that the $C_9$-and heavier stream or the $C_{12}$+ residual stream is processed using solvent extraction or solvent distillation with a polar solvent or stripping with steam or other media to separate highly condensed aromatics as a residual stream from $C_9$+ recycle to transalkylation.

The $C_8$-aromatics product recovered as streams 18, 38, 58 and 113, respectively, of FIGS. 1, 2, 3 and 4 may be further processed to recover valuable isomer products such as paraxylene. Such processing via adsorptive separation, crystallization and isomerization are described in U.S. Pat. No. 6,740,788, incorporated herein by reference thereto.

In the transalkylation unit represented in FIGS. 1, 2, 3 and 4 respectively as units 23, 46, 60 and 103, the feed is contacted with a transalkylation catalyst under transalkylation conditions to obtain a transalkylation product stream having an increased concentration of xylenes. The catalyst significantly comprises a UZM-14 aggregate material having unique properties of nanocrystallinity and porosity which permit the conversion of heavy aromatic feedstocks. Preferably the UZM-14 aggregate material comprises one or more of the following characteristics:

(1) globular aggregates have a mesopore volume of at least about 0.10 cc/gram, preferably at least about 0.13 cc/gram, and especially at least about 0.2 cc/gram;

(2) the UZM-14 crystallites have at least about $1 \times 10^{19}$ 12-ring-channel openings/gram of UZM-14 material;

(3) the mean crystallite length parallel to the direction of the 12-ring channels is about 60 nm or less and preferably about 50 nm or less;

(4) The $Si/Al_2$ ratio of the UZM-14 aggregate material generally is between about 8 and about 50, and preferably is no more than about 30.

The transalkylation catalyst employed in the schemes of FIGS. 1, 2, 3 and 4 preferably comprises a binder preferably comprising one or more of alumina, silica and silica-alumina and a metal component comprising one or more elements selected from groups VIB(6), VIIB(7), VIII(8-10), 1B(11) and IVA(14) of the Periodic Table. Preferably the metal component is selected from one or more of rhenium, nickel, cobalt, molybdenum and tungsten. Suitable metal amounts in the transalkylation catalyst range from about 0.01 to about 15 wt-% on an elemental basis, with the range from about 0.1 to about 10 wt-% being preferred, and the range from about 0.1 to about 6 wt-% being highly preferred. The catalyst also may comprise a phosphorus component, and an optional binder comprises aluminum phosphate as described in U.S. Pat. No. 6,008,423 which is incorporated herein by reference thereto. The catalyst also preferably has been subjected to a presulfiding step to incorporate from about 0.05 to about 2 wt.-% sulfur on an elemental basis.

The catalyst may be formed into any shape useful in the process of the invention, including but not limited to extrudates, spheres, pills, tablets, cakes, powders and granules. A spherical catalyst may be manufactured by the well known oil-drop method, described fundamentally in U.S. Pat. No. 2,620,314.

The transalkylation catalyst employed in the schemes of FIGS. 1, 2, 3 and 4 optionally may comprise an additional zeolitic component, The additional zeolite component preferably is selected from one or more of MFI, MEL, EUO, FER, MFS, MTT, MTWMWW, MAZ, TON and FAU (IUPAC Commission on Zeolite Nomenclature) and UZM-8 (see WO 2005/113439, incorporated herein by reference thereto). More preferably the additional zeolitic component consists essentially of MFI. Suitable total zeolite amounts in the catalyst range from about 1 to about 100 wt-%, preferably from about 10 to about 95 wt-%, and more preferably between about 75 and about 90 wt-%.

Conditions employed in the transalkylation zone normally include a temperature of from about 200° to about 540° C. The transalkylation zone is operated at moderately elevated pressures broadly ranging from about 100 kPa to about 6 Mpa absolute. The transalkylation reaction can be effected over a wide range of space velocities, with higher space velocities effecting a higher ratio of para-xylene at the expense of conversion. Liquid hourly space velocity generally is in the range of from about 0.1 to about 20 hr$^{-1}$. The feedstock is preferably transalkylated in the vapor phase and in the presence of hydrogen; if transalkylated in the liquid phase, then the presence of hydrogen is optional. If present, free hydrogen is associated with the feedstock and recycled hydrocarbons in an amount of about 0.1 moles per mole of alkylaromatics up to about 10 moles per mole of alkylaromatic. This ratio of hydrogen to alkylaromatic is also referred to as hydrogen to hydrocarbon ratio.

Example 1

A catalytic reformate feedstock was defined for yield comparisons based on component analyses performed in the laboratory and converted to a total feed of 650.05 metric tons/annum using toluene quantity as the base point:

| | |
|---|---|
| Pentanes | 17.0 |
| Hexanes | 38.0 |
| Benzene | 51.0 |
| Heptanes | 8.0 |
| Toluene | 100.0 |
| Octanes | 1.0 |
| $C_8$ Aromatics | 228.0 |
| $C_9$ Aromatics | 161.0 |
| $C_{10}$ Alkylaromatics | 22.0 |
| $C_{11}$ Alkylaromatics | 4.33 |
| $C_{12}$+ Alkylaromatics | 1.44 |
| Naphthalene | 0.96 |
| Methylnaphthalenes | 2.16 |
| $C_{12}$+ Naphthalenes | 12.51 |
| Biphenyls/Diphenyls/Fluorenes | 2.65 |

Example 2

Using data derived from laboratory tests on conversions of the various components of Example 1, yields were calculated based on the proportion of the $C_9$ and heavier stream that is fractionated prior to being sent to transalkylation. The total yield of benzene and $C_8$ aromatics is shown as the result and compared to yields according to the process of the known art:

| | % Fractionated | Yield, T/A |
|---|---|---|
| Known art | 100 | 538.3 |
| Invention | 100 | 548.6 |
| Invention | 75 | 550.6 |
| Invention | 50 | 553.3 |
| Invention | 25 | 556.9 |

The invention shows a clear advantage over the known art.

The above description and examples are intended to be illustrative of the invention without limiting its scope. The skilled routineer will readily understand how to extrapolate parameters of the disclosure to other embodiments of the invention. The invention is limited only by the claims set forth herein.

The invention claimed is:

1. A process for producing xylenes from an aromatics-rich feed stream comprising the steps of:

(a) separating the aromatics-rich feed stream and a transalkylation product stream in a fractionation zone to produce a benzene-rich stream, a toluene-rich stream, a C8-aromatics product and C9-and-heavier stream;

(b) fractionating the C9-and-heavier stream in a heavy-aromatics fractionator to obtain a C9-C11+ heavy transalkylation feed and a C12+ residual stream;

(c) combining the toluene-rich stream and C9-C11+ heavy transalkylation feed to obtain a combined transalkylation feed and contacting the combined feed in a transalkylation zone under transalkylation conditions with a transalkylation catalyst which comprises (1) an aggregate zeolitic material comprising globular aggregates of crystallites having a MOR framework type comprising 12-ring channels, a mesopore volume of at least about 0.10 cc/gram, a mean crystallite length parallel to the direction of the 12-ring channels of about 60 nm or less, the number of 12-ring channel-openings per gram of zeolite of at least $1\times10^{19}$, and a silica-alumina (Si/Al$_2$) mole ratio of from about 8 to about 50, (2) a binder comprising one or more of alumina, silica, silica-alumina, aluminum phosphate, and (3) a metal component selected from the group consisting of groups VIB(6), VIIB(7), VIII(8-10) and IVA(14) of the Periodic Table, and mixtures thereof, to produce the transalkylation product stream of step (a) having an increased concentration of xylenes relative to the combined transalkylation feed.

2. The process of claim 1 wherein the aromatics-rich feed stream comprises one or both of catalytic reformate and byproduct gasoline from the production of olefins.

3. The process of claim 1 wherein the aromatics-rich feed stream comprises hydrotreated light cycle oil.

4. The process of claim 1 wherein the combined transalkylation feed further comprises benzene.

5. The process of claim 1 wherein the transalkylation feed comprises aromatic compounds having from 2 to 4 rings.

6. The process of claim 1 wherein the transalkylation conditions comprise a temperature from about 200° C. to about 540° C., a pressure from about 100 kPa to about 6 MPa absolute, and a space velocity from about 0.1 to about 20 hr−1.

7. The process of claim 1 wherein the transalkylation catalyst further comprises an additional zeolitic component selected from the group consisting of one or more of MFI, MEL, EUO, FER, MFS, MTT, MTW, MWW, MAZ, TON, FAU and UZM-8.

8. The process of claim 7 wherein the additional zeolitic component consists essentially of MFI.

9. The process of claim 1 wherein the mean crystallite length parallel to the direction of the 12-ring channels is about 50 nm or less.

10. The process of claim 1 wherein the mesopore volume of the globular aggregates of crystallites is at least about 0.13 cc/gram.

11. The process of claim 1 further comprising passing the $C_8$-aromatics product to a combination of a para-xylene-recovery process and a $C_8$-aromatics-isomerization process to obtain a para-xylene product and a $C_7$-and-lighter stream sent to step (a) for separation of a benzene-rich stream, a toluene-rich stream, and a non-aromatic product.

12. The process of claim 1 further comprising dividing the $C_9$-and-heavier stream into a heavy recycle stream and a heavy-aromatics-fractionator feed stream and bypassing the heavy recycle stream directly to the transalkylation unit.

13. A process for producing xylenes from an aromatics-rich feed stream comprising the steps of:

(a) separating the aromatics-rich feed stream and a transalkylation product stream in a fractionation zone to produce a benzene-rich stream, a toluene-rich stream, a C8-aromatics product and C9-and-heavier stream, (b) combining the toluene-rich stream and C9-and-heavier stream to obtain a combined transalkylation feed and contacting the combined feed in a transalkylation zone under transalkylation conditions with a transalkylation catalyst which comprises (1) an aggregate zeolitic material comprising globular aggregates of crystallites having a MOR framework type comprising 12-ring channels, a mesopore volume of at least about 0.10 cc/gram, a mean crystallite length parallel to the direction of the 12-ring channels of about 60 nm or less, the number of 12-ring channel-openings per gram of zeolite of at least $1 \times 10^{19}$, and a silica-alumina ($Si/Al_2$) mole ratio of from about 8 to about 50, (2) a binder comprising one or more of alumina, silica, silica-alumina, aluminum phosphate, and (3) a metal component selected from the group consisting of groups VIB(6), VIIB(7), VIII(8-10) and IVA(14) of the Periodic Table, and mixtures thereof, to produce the transalkylation product stream of step (a) having an increased concentration of xylenes relative to the combined transalkylation feed.

14. The process of claim 13 wherein the mean crystallite length parallel to the direction of the 12-ring channels is about 50 nm or less.

15. A process for producing xylenes from an aromatics-rich feed stream comprising the steps of:

(a) combining the aromatics-rich feed stream with recycled heavy aromatics and a recycled toluene-rich stream to obtain a combined transalkylation feed and contacting the combined feed in a transalkylation zone under transalkylation conditions with a transalkylation catalyst which comprises (1) an aggregate zeolitic material comprising globular aggregates of crystallites having a MOR framework type comprising 12-ring channels, a mesopore volume of at least about 0.10 cc/gram, a mean crystallite length parallel to the direction of the 12-ring channels of about 60 nm or less, the number of 12-ring channel-openings per gram of zeolite of at least $1 \times 10^{19}$, and a silica-alumina ($Si/Al_2$) mole ratio of from about 8 to about 50, (2) a binder comprising one or more of alumina, silica, silica-alumina, aluminum phosphate, and (3) a metal component selected from the group consisting of groups VIB(6), VIIB(7), VIII(8-10) and IVA(14) of the Periodic Table, and mixtures thereof to produce a transalkylation product stream having an increased concentration of xylenes relative to the combined transalkylation feed;

(b) separating the transalkylation product stream in a fractionation zone to produce a benzene-rich stream, a toluene-rich recycle stream, a C8-aromatics product and C9-and-heavier stream; and (c) fractionating the C9-and-heavier stream in a heavy-aromatics fractionator to obtain recycled heavy aromatics and a C12+ residual product stream.

16. The process of claim 15 wherein the mean crystallite length parallel to the direction of the 12-ring channels is about 50 nm or less.

* * * * *